US011885752B2

(12) United States Patent
St-Aubin et al.

(10) Patent No.: US 11,885,752 B2
(45) Date of Patent: Jan. 30, 2024

(54) CALIBRATION METHOD AND DEVICE THEREFOR

(71) Applicant: Rapiscan Holdings, Inc., Hawthorne, CA (US)

(72) Inventors: Emmanuel St-Aubin, St-Laurent (CA); Philippe Desjeans-Gauthier, St-Laurent (CA); Ola El Bakry, St-Laurent (CA); Simon Archambault, St-Laurent (CA); William Awad, St-Laurent (CA)

(73) Assignee: Rapiscan Holdings, Inc., Hawthorne, CA (US)

( * ) Notice: Subject to any disclaimer, the term of this patent is extended or adjusted under 35 U.S.C. 154(b) by 0 days.

(21) Appl. No.: 17/363,950

(22) Filed: Jun. 30, 2021

(65) Prior Publication Data

US 2023/0000459 A1 Jan. 5, 2023

(51) Int. Cl.
*G01N 23/00* (2006.01)
*G01N 23/04* (2018.01)
(Continued)

(52) U.S. Cl.
CPC ........... *G01N 23/04* (2013.01); *G01N 23/087* (2013.01); *G01N 23/10* (2013.01); *G01V 5/0041* (2013.01);
(Continued)

(58) Field of Classification Search
None
See application file for complete search history.

(56) References Cited

U.S. PATENT DOCUMENTS 4,020,346 A 4/1977 Dennis
4,618,978 A * 10/1986 Cosman ............... G01N 23/046
324/309

(Continued)

FOREIGN PATENT DOCUMENTS

CA 1301371 5/1992
CA 2163884 12/1994
(Continued)

OTHER PUBLICATIONS

International Search Report for International Application No. PCT/CA2019/051489, dated Dec. 30, 2019, (pp. 4).
(Continued)

*Primary Examiner* — Thomas R Artman
(74) *Attorney, Agent, or Firm* — Novel IP

(57) ABSTRACT

A method of determining at least one x-ray scanning system geometric property includes the steps of positioning a calibration device inside a scanning chamber of the scanning device, the chamber being intersected by at least one fan beam of x-rays during a scanning operation, measuring a distance between the calibration device and at least one inner wall of the chamber, scanning the calibration device to produce an image of the calibration device, identifying pixels representing the a geometric feature of the calibration device in the image, determining a position and orientation of the pixels representing the geometric feature in the image and, determining a scanning system property based on the position and orientation of the pixels representing the geometric feature in the image. The position and orientation of the feature in the scanning chamber and the x-ray scanning system property may be determined simultaneously.

13 Claims, 11 Drawing Sheets

(51) Int. Cl.
*G01N 23/087* (2018.01)
*G01N 23/10* (2018.01)
*G01V 5/00* (2006.01)

(52) U.S. Cl.
CPC . *G01N 2223/04* (2013.01); *G01N 2223/1016* (2013.01); *G01N 2223/206* (2013.01); *G01N 2223/3035* (2013.01); *G01N 2223/3307* (2013.01); *G01N 2223/3308* (2013.01); *G01N 2223/41* (2013.01); *G01N 2223/424* (2013.01); *G01N 2223/5015* (2013.01); *G01N 2223/639* (2013.01); *G01N 2223/643* (2013.01)

(56) References Cited

U.S. PATENT DOCUMENTS

| | | | |
|---|---|---|---|
| 4,872,188 A * | 10/1989 | Lauro | H04N 5/3205 |
| | | | 378/18 |
| 5,532,492 A | 7/1996 | He | |
| 5,541,856 A | 7/1996 | Hammermeister | |
| 5,600,700 A | 2/1997 | Krug | |
| 5,768,334 A | 6/1998 | Maitrejean | |
| 5,838,758 A | 11/1998 | Krug | |
| 5,872,829 A * | 2/1999 | Wischmann | A61B 6/583 |
| | | | 378/20 |
| 5,974,111 A | 10/1999 | Krug | |
| 6,005,912 A | 12/1999 | Ocleppo | |
| 6,018,562 A | 1/2000 | Willson | |
| 6,058,159 A | 5/2000 | Conway | |
| 6,081,580 A | 6/2000 | Grodzins | |
| 6,218,943 B1 | 4/2001 | Ellenbogen | |
| 6,304,629 B1 | 10/2001 | Conway | |
| 6,379,043 B1 * | 4/2002 | Zylka | G01N 23/044 |
| | | | 378/207 |
| 6,453,003 B1 | 9/2002 | Springer | |
| 6,453,007 B2 | 9/2002 | Adams | |
| 6,490,477 B1 * | 12/2002 | Zylka | A61B 6/583 |
| | | | 600/417 |
| 6,590,956 B2 | 7/2003 | Fenkart | |
| 6,895,072 B2 | 5/2005 | Schrock | |
| 6,928,137 B2 | 8/2005 | Bruder | |
| 6,993,111 B1 | 1/2006 | Annis | |
| 7,020,241 B2 | 3/2006 | Beneke | |
| 7,062,011 B1 | 6/2006 | Tybinkowski | |
| 7,139,406 B2 | 11/2006 | McClelland | |
| 7,158,611 B2 | 1/2007 | Heismann | |
| 7,162,005 B2 | 1/2007 | Bjorkholm | |
| 7,164,750 B2 | 1/2007 | Nabors | |
| 7,221,732 B1 | 5/2007 | Annis | |
| 7,319,737 B2 | 1/2008 | Singh | |
| 7,339,159 B2 * | 3/2008 | Juh | A61B 6/583 |
| | | | 378/207 |
| 7,384,194 B2 | 6/2008 | Gatten | |
| 7,417,440 B2 | 8/2008 | Peschmann | |
| 7,453,987 B1 | 11/2008 | Richardson | |
| 7,486,772 B2 | 2/2009 | Lu | |
| 7,579,845 B2 | 8/2009 | Peschmann | |
| 7,606,348 B2 | 10/2009 | Foland | |
| 7,634,051 B2 | 12/2009 | Robinson | |
| 7,636,418 B2 | 12/2009 | Anwar | |
| 7,656,995 B2 | 2/2010 | Robinson | |
| 7,672,427 B2 | 3/2010 | Chen | |
| 7,693,261 B2 | 4/2010 | Robinson | |
| 7,706,507 B2 | 4/2010 | Williamson | |
| 7,734,066 B2 | 6/2010 | Delia | |
| 7,831,012 B2 | 11/2010 | Foland | |
| 7,873,201 B2 | 1/2011 | Eilbert | |
| 7,876,879 B2 | 1/2011 | Morton | |
| 7,945,017 B2 | 5/2011 | Chen | |
| 8,009,799 B2 | 8/2011 | Doyle | |
| 8,009,800 B2 | 8/2011 | Doyle | |
| 8,014,493 B2 | 9/2011 | Roux | |
| 8,031,903 B2 | 10/2011 | Paresi | |
| 8,098,794 B1 | 1/2012 | Fernandez | |
| 8,116,428 B2 | 2/2012 | Gudmundson | |
| 8,138,770 B2 | 3/2012 | Peschmann | |
| D658,294 S | 4/2012 | Awad | |
| 8,189,889 B2 * | 5/2012 | Pearlstein | G06T 11/003 |
| | | | 382/128 |
| 8,233,588 B2 | 7/2012 | Gibson | |
| 8,284,896 B2 | 10/2012 | Singh | |
| 8,311,309 B2 | 11/2012 | Siedenburg | |
| 8,320,523 B2 | 11/2012 | Zhang | |
| 8,401,270 B2 | 3/2013 | Eilbert | |
| 8,428,217 B2 | 4/2013 | Peschmann | |
| 8,478,016 B2 | 7/2013 | Robinson | |
| 8,515,010 B1 | 8/2013 | Hurd | |
| 8,537,968 B2 | 9/2013 | Radley | |
| 8,674,706 B2 | 3/2014 | Peschmann | |
| 8,774,357 B2 | 7/2014 | Morton | |
| 8,781,066 B2 | 7/2014 | Gudmundson | |
| 8,831,331 B2 | 9/2014 | Gudmundson | |
| 8,867,816 B2 | 10/2014 | Bouchard | |
| 8,879,791 B2 | 11/2014 | Drouin | |
| 9,042,511 B2 | 5/2015 | Peschmann | |
| 9,170,212 B2 | 10/2015 | Bouchard | |
| 9,189,846 B2 | 11/2015 | Wismüller | |
| 9,194,975 B2 | 11/2015 | Drouin | |
| 9,196,082 B2 * | 11/2015 | Pearlstein | A61N 5/1049 |
| 9,268,058 B2 | 2/2016 | Peschmann | |
| 9,311,277 B2 | 4/2016 | Rinkel | |
| 9,681,851 B2 * | 6/2017 | Rohler | A61B 6/032 |
| 9,746,431 B2 * | 8/2017 | Grader | G01N 23/046 |
| 9,823,383 B2 | 11/2017 | Hanley | |
| 9,989,508 B2 | 6/2018 | Awad | |
| 10,089,956 B2 | 10/2018 | Awad | |
| 10,180,483 B2 * | 1/2019 | Holdsworth | A61B 6/032 |
| 10,254,436 B2 | 4/2019 | Awad | |
| 10,510,319 B2 | 12/2019 | Awad | |
| 10,555,716 B2 * | 2/2020 | Rohler | A61B 6/583 |
| 10,557,911 B2 * | 2/2020 | Holdsworth | A61B 6/032 |
| 10,650,783 B2 | 5/2020 | Awad | |
| 10,795,047 B2 | 10/2020 | St-Aubin | |
| 10,795,048 B2 | 10/2020 | St-Aubin | |
| 10,795,049 B2 | 10/2020 | St-Aubin | |
| 10,809,414 B2 | 10/2020 | St-Aubin | |
| 10,901,114 B2 | 1/2021 | St-Aubin | |
| 11,116,471 B2 * | 9/2021 | Rohler | A61B 6/586 |
| 11,478,214 B2 * | 10/2022 | Siewerdsen | A61B 6/584 |
| 2001/0014137 A1 | 8/2001 | Bjorkholm | |
| 2003/0085348 A1 | 5/2003 | Megerle | |
| 2004/0091078 A1 | 5/2004 | Ambrefe | |
| 2004/0179643 A1 | 9/2004 | Gregerson | |
| 2005/0008126 A1 * | 1/2005 | Juh | A61B 6/037 |
| | | | 250/252.1 |
| 2005/0025280 A1 | 2/2005 | Schulte | |
| 2005/0058242 A1 | 3/2005 | Peschmann | |
| 2005/0117700 A1 | 6/2005 | Peschmann | |
| 2006/0098866 A1 | 5/2006 | Whitson | |
| 2007/0003009 A1 | 1/2007 | Gray | |
| 2007/0116177 A1 * | 5/2007 | Chen | A61B 6/027 |
| | | | 378/57 |
| 2007/0132580 A1 | 6/2007 | Ambrefe | |
| 2007/0133742 A1 | 6/2007 | Gatten | |
| 2007/0172129 A1 | 7/2007 | Tortora | |
| 2007/0235652 A1 | 10/2007 | Smith | |
| 2007/0280502 A1 | 12/2007 | Paresi | |
| 2008/0025470 A1 | 1/2008 | Streyl | |
| 2008/0063140 A1 | 3/2008 | Awad | |
| 2009/0010386 A1 | 1/2009 | Peschmann | |
| 2009/0060135 A1 | 3/2009 | Morton | |
| 2009/0196396 A1 | 8/2009 | Doyle | |
| 2009/0285353 A1 | 11/2009 | Ellenbogen | |
| 2010/0002834 A1 | 1/2010 | Gudmundson | |
| 2010/0027741 A1 | 2/2010 | Doyle | |
| 2010/0086185 A1 | 4/2010 | Weiss | |
| 2010/0098218 A1 | 4/2010 | Vermilyea | |
| 2010/0207741 A1 | 8/2010 | Gudmundson | |
| 2010/0208972 A1 | 8/2010 | Bouchard | |
| 2010/0223016 A1 | 9/2010 | Gibson | |
| 2010/0295689 A1 | 11/2010 | Armistead, Jr. | |
| 2010/0302034 A1 | 12/2010 | Clements | |
| 2011/0007870 A1 | 1/2011 | Roux | |
| 2011/0019797 A1 | 1/2011 | Morton | |

(56) References Cited

U.S. PATENT DOCUMENTS

| | | |
|---|---|---|
| 2011/0033118 A1 | 2/2011 | Yildiz |
| 2011/0172972 A1 | 7/2011 | Gudmundson |
| 2011/0228896 A1 | 9/2011 | Peschmann |
| 2011/0235777 A1 | 9/2011 | Gozani |
| 2012/0069964 A1 | 3/2012 | Scholling |
| 2012/0093367 A1 | 4/2012 | Gudmundson |
| 2012/0140879 A1 | 6/2012 | Gudmundson |
| 2012/0230463 A1 | 9/2012 | Morton |
| 2012/0275646 A1 | 11/2012 | Drouin |
| 2013/0034268 A1 | 2/2013 | Perron |
| 2013/0085788 A1 | 4/2013 | Rowlan |
| 2013/0114788 A1 | 5/2013 | Crass |
| 2013/0163811 A1 | 6/2013 | Oelke |
| 2013/0294574 A1 | 11/2013 | Peschmann |
| 2013/0301794 A1* | 11/2013 | Grader .......... G01N 23/087 378/5 |
| 2013/0336447 A1 | 12/2013 | Morton |
| 2014/0072108 A1* | 3/2014 | Rohler .......... A61B 6/032 378/207 |
| 2014/0185923 A1 | 7/2014 | Chen |
| 2014/0205059 A1 | 7/2014 | Sharpless |
| 2014/0211917 A1 | 7/2014 | Chen |
| 2014/0211980 A1 | 7/2014 | Bouchard |
| 2014/0222385 A1 | 8/2014 | Muenster |
| 2014/0241495 A1 | 8/2014 | Gudmundson |
| 2014/0249536 A1* | 9/2014 | Jajeh .......... A61B 17/72 606/96 |
| 2015/0021342 A1 | 1/2015 | Crass |
| 2015/0186732 A1 | 7/2015 | Perron |
| 2015/0268016 A1 | 9/2015 | Eshetu |
| 2015/0282781 A1* | 10/2015 | Rohler .......... A61B 6/582 378/207 |
| 2015/0355117 A1 | 12/2015 | Morton |
| 2016/0025888 A1 | 1/2016 | Peschmann |
| 2016/0252647 A1 | 9/2016 | Awad |
| 2017/0103513 A1 | 4/2017 | Heilmann |
| 2017/0184756 A1 | 6/2017 | Miao |
| 2017/0236232 A1 | 8/2017 | Morton |
| 2017/0309043 A1 | 10/2017 | Li |
| 2017/0319169 A1* | 11/2017 | Rohler .......... A61B 6/586 |
| 2017/0328844 A1 | 11/2017 | Li |
| 2017/0371010 A1 | 12/2017 | Shanbhag |
| 2018/0106733 A1 | 4/2018 | Li |
| 2018/0162584 A1 | 6/2018 | Tauber |
| 2019/0346379 A1 | 11/2019 | Awad |
| 2019/0346381 A1 | 11/2019 | Awad |
| 2020/0085404 A1* | 3/2020 | Siewerdsen .......... G06T 7/60 |
| 2020/0103548 A1 | 4/2020 | Yu |
| 2020/0110043 A1 | 4/2020 | Marín |
| 2020/0146648 A1* | 5/2020 | Rohler .......... A61B 6/582 |
| 2021/0361254 A1* | 11/2021 | Rohler .......... A61B 6/586 |
| 2021/0381991 A1* | 12/2021 | Desjeans-Gauthier .......... G01N 23/10 |
| 2023/0000459 A1* | 1/2023 | St-Aubin .......... G01N 23/087 |

FOREIGN PATENT DOCUMENTS

| | | | |
|---|---|---|---|
| CA | 2574402 | | 1/2006 |
| CA | 2744690 | | 6/2009 |
| CA | 2692662 | | 3/2010 |
| CA | 2697525 | | 3/2010 |
| CA | 2709468 | | 3/2010 |
| CA | 2690163 | | 8/2011 |
| CA | 2869201 | | 10/2013 |
| CN | 102175698 | | 9/2011 |
| CN | 103327901 | | 9/2013 |
| CN | 104165896 | | 11/2014 |
| CN | 108937992 A * | 12/2018 | .......... A61B 6/44 |
| CN | 114767137 A * | 7/2022 | |
| CN | 116359257 A * | 6/2023 | |
| FR | 3037401 | | 12/2016 |
| JP | 3946612 | | 7/2007 |
| WO | 9423458 | | 10/1994 |
| WO | 2006137919 | | 12/2006 |
| WO | 2008133765 | | 11/2008 |
| WO | WO-2008139167 A2 * | 11/2008 | .......... A61B 6/583 |
| WO | 2008157843 | | 12/2008 |
| WO | 2009114928 | | 9/2009 |
| WO | 2010025538 A1 | | 3/2010 |
| WO | 2013149788 | | 10/2013 |
| WO | 2018121444 | | 7/2018 |

OTHER PUBLICATIONS

International Search Report for International Application No. PCT/CA2013/050744, dated Jun. 10, 2014, (5 pages).

K. Wells; D.A. Bradley;, "A review of X-ray explosives detection techniques for checked baggage", Applied Radiation and Isotopes., Elsevier, Oxford., GB, GB, (Jan. 12, 2012), vol. 70, No. 8, doi:10.1016/j.apradiso.2012.01.011, ISSN 0969-8043, pp. 1729-1746, XP028401820.

Richard D. R. MacDonald, "<title>Design and implementation of a dual-energy x-ray imaging system for organic material detection in an airport security application</title>", Proceedings of SPIE, SPIE, (Apr. 4, 2001), vol. 4301, doi:10.1117/12.420922, ISSN 0277786X, pp. 31-41, XP055104503.

International Search Report for corresponding International Patent Application No. PCT/CA2014/050981 dated Jan. 5, 2015, 6 pgs.

International Search Report for corresponding International Patent Application No. PCT/CA2014/051074 dated Jan. 20, 2015.

International Search Report & Written Opinion for PCT/CA2019/050616, dated Jul. 5, 2019, (15 pages).

International Search Report and Written for International Application No. PCT/CA2018/051673, dated Mar. 14, 2019, (8-pages).

Lehmann et al., Generalized image combinations in dual KVP digital radiography, Medical Physics, Sep. 1981, 659-667, 8-5, American Association of Physicists in Medicine.

Bond et al., ZeCalc Algorithm Details, Lawrence Livermore National Laboratory, Jan. 7, 2013, Livermore U.S.A.

International Search Report and Written Opinion for International Application No. PCT/CA2019/050617, dated Jul. 30, 2019, (11 pages).

International Search Report and Written Opinion for International Application No. PCT/CA2018/051674, dated Mar. 29, 2019, (8 pages).

Hassanpour et al.(NPL "Illicit Material Detection using Dual-Energy X-ray Images", The International Arab Journal of Information Technology, vol. 13, No. 4, Jul. 2016, p. 8) (Year: 2016).

International Search Report and Written Opinion for International Application No. PCT/CA2018/051675, dated Mar. 21, 2019, (11 pages).

International Search Report and Written Opinion for International Application No. PCT/CA2018/051676, dated Mar. 26, 2019, (7 pages).

Hurd et al (U.S. Pat. No. 8,515,010, hereafter referred to as Hurd), Ying et al ("Dual Energy Volumetric X-ray Tomographic Sensor for Luggage Screening", IEEE, SAS Feb. 2007) (Year: 2007).

International Search Report and Written Opinion for International Application No. PCT/CA2018/051677, dated Mar. 29, 2019, (8 pages).

International Search Report and Written Opinion for International Application No. PCT/CA2020/051239, dated Dec. 16, 2020, (17 pages).

\* cited by examiner

CALIBRATION METHOD AND DEVICE THEREFOR

FIELD

The present invention relates to x-ray scanning devices and in particular to a device and method for determining calibration information for x-ray scanning devices.

BACKGROUND

Dual-energy x-ray scanning devices are often used to identify the physical and chemical characteristics of objects which may be unidentifiable by other means or which may be concealed by other objects. Such systems emit x-rays from an x-ray source which are detected by detectors. The system subsequently converts the analog signal from the detectors to a digital signal which may be read as data by computerized components of the system. Such data may be input into one or more algorithms which facilitate the identification of the scanned object and one or more of its physical or chemical characteristics.

Any algorithm attempting to determine any geometrical features based on the analysis of a set of dual-energy images acquired by a dual-energy x-ray scanning device requires the knowledge of the path followed by the neutral particles, such as photons or neutrons, for example, contributing to the signal of all pixels in each of the dual-energy images. This can be decomposed into two different types of information, namely the positions of the sources and the detectors emitting and receiving the neutral particles and the mapping of the detectors indexing to the pixels of the images. In order to ensure that the dual-energy x-ray images are reliable, it is advantageous to account for the real positions of the source and detectors in the x-ray scanning system.

A path is considered as the orientation in 3D space of a vector linking the positions of a source, interpreted as a first point or "point source", and a detector, interpreted as a second point or "point detector". In operation, x-rays are emitted in all directions from the source and accordingly, portions of each detector will be encountered by a plurality of x-rays to generate a pixel. To accommodate algorithms working with this extended body of x-rays being sent from the source and received by the detector, the set of x-rays contributing to a pixel may be considered in unison or as a set of points. For point-source of neutral particles and detector arrays used in most imaging applications, it is common to neglect the contribution of the scattered particles to the transmission images and therefore, to assume that all particles contributing to the signal of a given pixel have travelled on the same path.

Usually, the designing process of an imaging device specifies the positions of the sources and detectors in such a way as to achieve certain specifications or performances. However, there are many sources of uncertainties during the manufacturing and fielding processes which may lead to significant differences between the expected and the actual positions of the sources and detectors. Mechanical tolerances, assembly techniques, shipping and handling of the device, for example, may all introduce uncertainties in the source and detector positions. Large position differences would cause sufficiently large losses of performance that they should be noticed during facility or commissioning tests. However, small differences between the expected and actual positions of the source and detectors may not be perceived by conventional procedures. In these cases, even if the imaging device may be able to produce good quality images, the uncertainties in the travel path of the particles may result in significant errors in the output of the aforementioned algorithms such as, for example, image artifacts or warping.

Measurement tools are available to determine with a degree of precision the position and orientation of each source and detector in a system. However, many x-ray scanning devices are assembled in a manner wherein either the source(s), the detector(s) or both are concealed. Therefore, it may be impossible to perform direct measurements with any suitable measuring devices to determine the actual path of the particles once the device is commissioned. In such situations, there are no reliable means to measure the differences between the expected and actual positions of the sources and detectors. Accordingly, the manufacturers of such imaging devices are unaware of how their quality assurance procedures actually perform with regard to the geometry of the assembled system, or equivalently, the manufacturers do not know the actual quality of the assembly of the devices being sold and guaranteed to clients.

It is therefore desirable to have means of compensating for image quality loss due to differences between the expected and actual positions of at least one of the source(s) and the detector(s) of an x-ray scanning device wherein such means do not rely on direct measurement of the source(s) and/or detector(s).

SUMMARY

The present invention relates to x-ray scanning devices and in particular to a device and method for determining calibration information for x-ray scanning devices. One aspect proposed herein is to determine estimates of the actual source positions and detector positions of the assembly and the orientation of fan beams extending therebetween by analyzing images of a geometric calibration tool acquired by a commissioned x-ray imaging device and some direct measurements performed on at least one of the calibration tool itself or the system formed by the tool and the imaging device, but not on the sources and detectors themselves.

Preferably, the calibration tool is rigid and has geometric features that can be easily identified in the dual-energy images produced by the x-ray scanner and on the calibration tool itself. The geometric features are used as points of reference for positioning the calibration tool with respect to the imaging device in 3D space and in the images of the calibration tool produced by the imaging device.

In one aspect, there is provided a method of determining at least one x-ray scanning system geometric property including the steps of positioning a calibration device inside a scanning chamber of the x-ray scanning device, the scanning chamber being intersected by at least one fan beam of x-rays during a scanning operation, measuring a distance between the calibration device and at least one inner wall of the scanning chamber, scanning the calibration device to produce at least one image of the calibration device, identifying pixels representing the at least one geometric feature of the calibration device in the at least one image, determining a position and orientation of the pixels representing the at least one geometric feature in the at least one image and, determining at least one x-ray scanning system property based on the position and orientation of the pixels representing the at least one geometric feature in the at least one image. The position and orientation of the at least one feature in the scanning chamber and the at least one x-ray scanning system property may be determined simultaneously.

Determining the position of the at least one feature may further include the steps of determining an orientation of the at least one feature on the calibration device, in the at least one image, determining a length of a projection of pixels representing the at least one feature on an axis parallel with a direction of displacement through the scanning chamber, and using the orientation of the at least one feature and the length of the projection to determine an actual length of the at least one feature.

The method may further include the step of performing a least squares analysis to solve for the at least one x-ray scanning system property which, together with the orientation of the at least one feature, minimizes a difference between one of a distance, a position and an orientation of geometric features as represented in the at least one image of the calibration device and the geometric features of the calibration device.

The at least one x-ray scanning system property may include at least one of an angle of the at least one fan beam and a distance between an x-ray emission source and an array of x-ray detectors between which the fan beam extends during a scanning operation. The angle of the fan beam and the distance between the x-ray emission source and the array of detectors may both be determined simultaneously.

The pixels representing the at least one feature of the calibration device may be pixels representing one of a vertex and an edge. The vertex may include pixels representing an end point of a wire used to construct the calibration device and the edge includes pixels representing a length of wire extending from at least one end point of the wire used to construct the calibration device.

In another aspect, the at least one fan beam includes two fan beams. The two fan beams may be spaced apart along a horizontal axis corresponding with a direction of displacement through the scanning chamber. One of the two fan beams may intersect the scanning chamber from beneath a displacement assembly extending through the scanning chamber and the other one of the two fan beams may intersect the scanning chamber from a first side of the displacement assembly toward a second side of the displacement assembly.

In another aspect, there is provided a calibration device for use with an x-ray scanning device. The device includes a base and a frame extending upwardly relative to the base. At least one first attachment portion is coupled with at least one of a base portion and a frame portion. At least one second attachment portion is coupled with another frame portion. At least one wire extends between one first attachment portion and one second attachment portion. The at least one wire, when scanned by an x-ray scanning system, produces image pixels representing at least one geometric feature for use in determining at least one x-ray scanning system property.

A plurality of first attachment portions may be interspersed about the base portion and the frame portion. A plurality of second attachment portions may be interspersed about the frame portion. The device may further include a plurality of wires wherein each wire extends between a corresponding one of the first attachment portions and a corresponding one of the second attachment portions.

The frame may include a plurality of projections each having coupled therewith at least one of a first attachment portion of the plurality of first attachment portions and a second attachment portion of the plurality of second attachment portions. At least two projections of the plurality of projections may be joined at one end portion thereof.

The base may be rectangular and may have an aperture therethrough for reducing obstruction of x-rays passing through the calibration device during a scanning operation.

BRIEF DESCRIPTION OF THE DRAWINGS

Exemplary non-limiting aspects are described with reference to the accompanying drawings in which.

DESCRIPTION

The present invention relates to x-ray scanning devices and in particular to a device and method for determining calibration information for x-ray scanning devices.

Scanning the calibration device in an x-ray scanning device can provide calibration information relating to the actual positions of the source(s) and detector(s) of that scanner in accordance with the aspects described herein.

Figure 1:
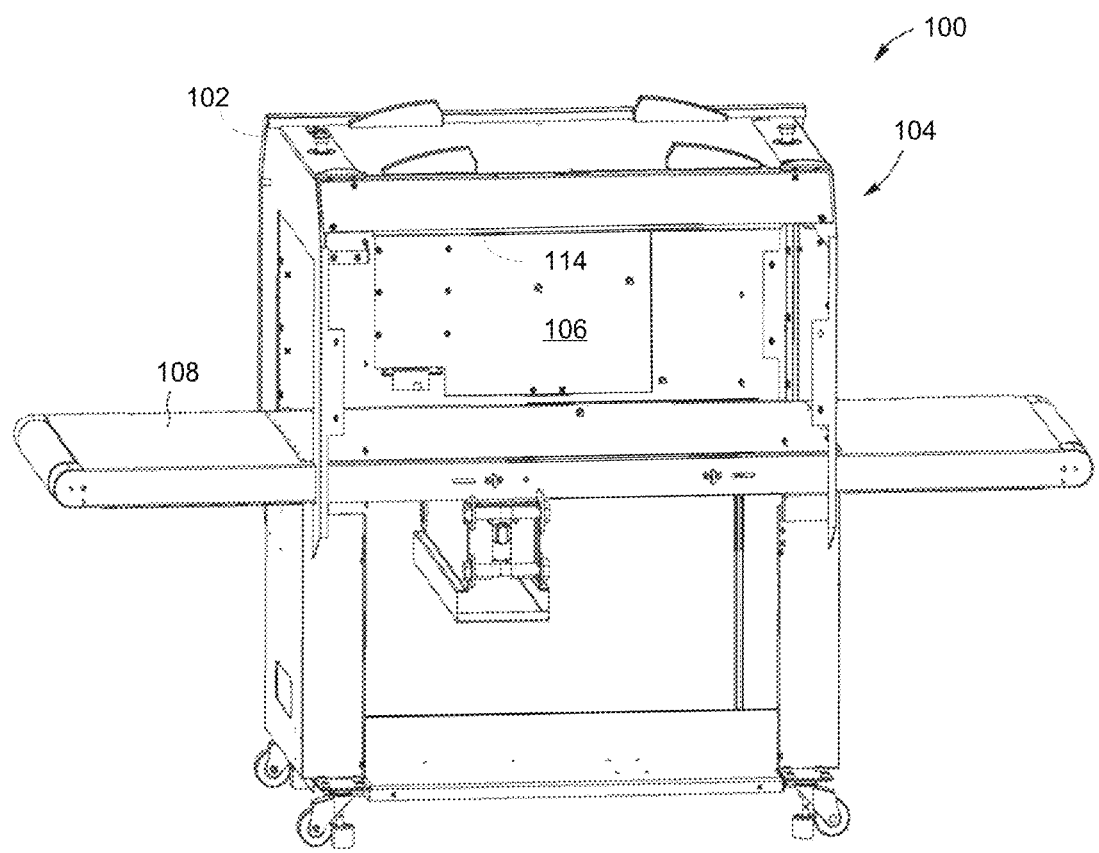
FIG. 1 is an illustration of an exemplary x-ray scanning device which may be used in accordance with the present invention.

According to the aspect shown in FIG. 1, there is provided an exemplary x-ray scanning device or system 100. The x-ray scanning device 100 includes a housing 102 having openings 104 at either end thereof. The openings 104 provide access to a scanning chamber 106 passing through the housing 102. The system 100 may further include a displacement assembly 108, such as a conveyor, which extends through the scanning chamber 106 and which may be used to displace at least one object of interest to be scanned using the x-ray scanning device 100.

Figure 2:
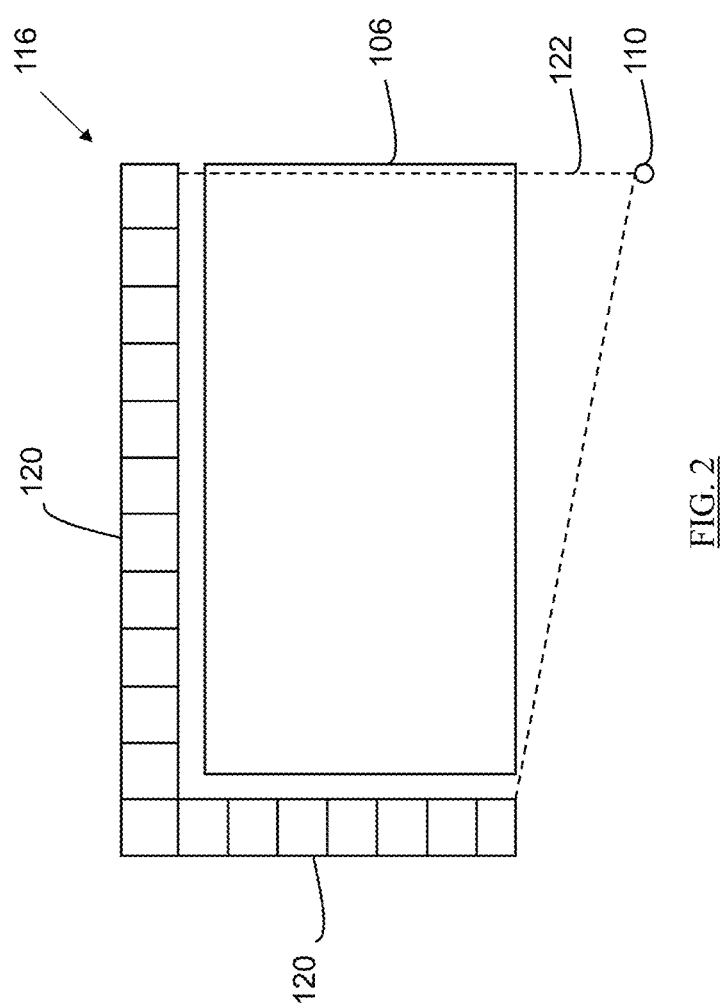
FIG. 2 is an illustration of a source relative to a detector array.
Figure 3:
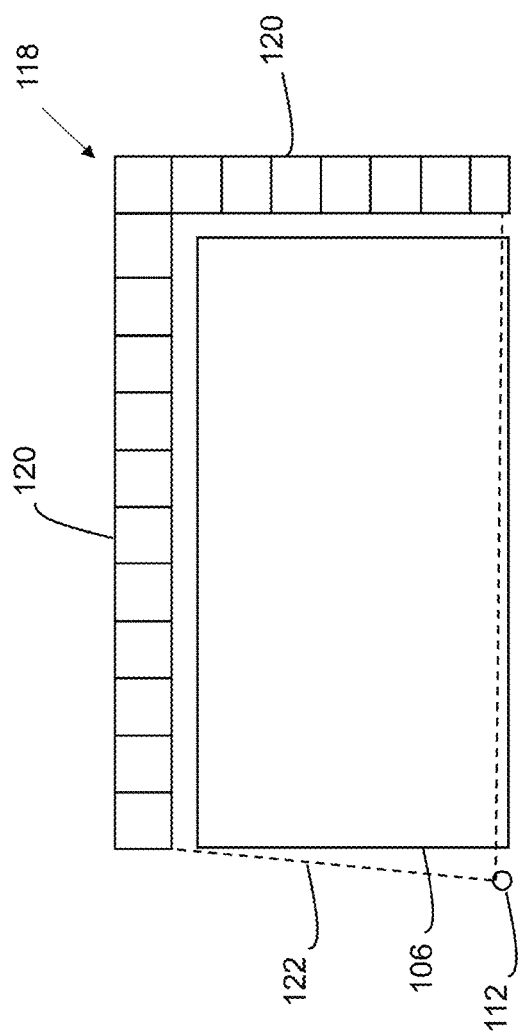
FIG. 3 is an illustration of a second source relative to a second detector array.

Located within the scanning chamber 106 are source assembly 110 and source assembly 112, which are shown in FIG. 2 and FIG. 3. Source assemblies 110 and 112 each include a source (not shown) for emitting electromagnetic radiation such as x-rays, preferably in a fan-shaped beam 122.

In a constructed x-ray scanning device 100, source assembly 110 is preferably positioned beneath the displacement assembly 108 so that the fan beam emitted therefrom is projected from beneath the displacement assembly 108 and toward a top wall 114 (FIG. 1) of scanning chamber 106. Preferably, the fan beam is emitted in a substantially vertical direction. However, it should be understood that the fan beam may be projected at an angle which is offset from a strictly vertical direction. The fan beam of source assembly 112 preferably positioned beside the scanning chamber 106 so that the fan beam emitted therefrom is projected from one side of the displacement assembly 108 toward the other side of displacement assembly 108. Preferably, the fan beam is emitted at an angle of approximately 20 degrees. However, it should be understood that the fan beam may be projected at other angles.

In a constructed scanning device 100, the actual orientation of each of the fan beams may not necessarily be in perfect agreement with construction specifications and so determination of actual x-ray scanning system geometry is required for more accurate image output from the scanning device 100, in accordance with methods described further hereinafter.

As is further illustrated in FIG. 2 and FIG. 3, x-ray scanning device 100 further includes two arrays of detectors 116 (FIG. 2) and 118 (FIG. 3), each including at least one detector 120 and preferably a plurality of detectors 120 for receiving x-ray radiation emitted from a corresponding one of the source assemblies 110 and 112. For illustrative purposes, x-ray radiation emitted from source assembly 110 is received by detectors 120 of array 116 and x-ray radiation emitted from source assembly 112 is received by detectors 120 of array 118. In one aspect, the detector arrays 116, 118 are L-shaped and are positioned within or about the scanning chamber 106. The arrays 116, 118 do not have to be L-shaped as shown in FIGS. 2 and 3. Rather, the arrays 116, 118 may be linear or arcuate, or any other suitable shape.

The source assemblies 110 and 112 are axially spaced apart relative the direction of displacement through the scanning chamber 106 by the displacement assembly 108. Correspondingly, detector arrays 116 and 118 are also preferably axially spaced apart relative the direction of displacement through the scanning chamber 106 by the displacement assembly 108.

Utilization of multiple source assemblies spaced about the scanning chamber 106 at different positions and each paired with a corresponding detector array permits for acquisition of dual-energy data from multiple angles during a single scanning operation. Hence, this provides advantage in increased dual-energy data to be used by reconstruction algorithms to construct more reliable images of a scanned object.

In a scanning operation, x-rays are emitted by the source of each source assembly and pass through the scanning chamber 106 to be received by detectors 120 in the detector arrays 116, 118. Where an object is being scanned, the x-rays will also pass through the object being scanned before encountering one of the detectors 120 in the detector array 116, 118 for at least a portion of the scanning operation. Each detector 120 of the detector arrays 116, 118 generates signals in response to the x-rays they encounter. The signals are digitized and transmitted from the detector array to at least one processor and/or a data management system (DMS) in the form of raw dual-energy data. Such a DMS may, for example, be a cloud-based system or other remote system that is able to collect raw data from one or multiple x-ray scanning devices for singular or multilateral processing and analysis. The dual-energy data may be provided to any number of algorithms for processing. Preferably, the dual-energy data is provided, either directly or via retrieval from storage, to an object reconstruction algorithm which analyzes the raw data to reconstruct a representation of the scanned object. Further analysis at the raw data level may be undertaken or the representation of the object may provide a basis to generate one or more images of the object via reconstruction. Such raw data may also be transmitted to another location or module for further processing and/or analysis. It should therefore be understood that storage and/or processing of the data acquired by the detectors is not necessarily local to the scanning device.

X-rays emitted from source assembly to detector follow a path, which is the orientation in 3D space of a vector linking the positions of a source, interpreted as a first point or "point source", and a detector, interpreted as a second point or "point detector". In operation, x-rays are emitted in all directions from the source and accordingly, portions of each detector will be encountered by a plurality of x-rays. To accommodate algorithms working with this extended body of x-rays being sent from the source and received by the detector, the set of x-rays may be considered in unison or as a set of points. Accordingly, a set of x-rays may also be interpreted as following a path.

Acquisition of calibration data in order to determine actual x-ray scanning system geometry is performed by conducting a scanning operation on a calibration device. Preferably, the calibration device is rigid and presents a plurality of geometric features that can be easily identified both on the physical calibration device and in the dual-energy data images output by a scanning operation on the calibration device. The geometric features are used as reference points for positioning the calibration tool in the 3D space within the scanning chamber 106 of the scanning device 100 and in the images of the calibration device produced by the scanning operation. Measurements are performed on the geometric features using suitable measuring devices. The dimensions of the calibration device and its shape with respect to the geometric features are also measurable with suitable measuring devices. The actual position of the calibration device within the space of the scanning chamber 106 is estimated on the basis of those measurements.

Figure 4:
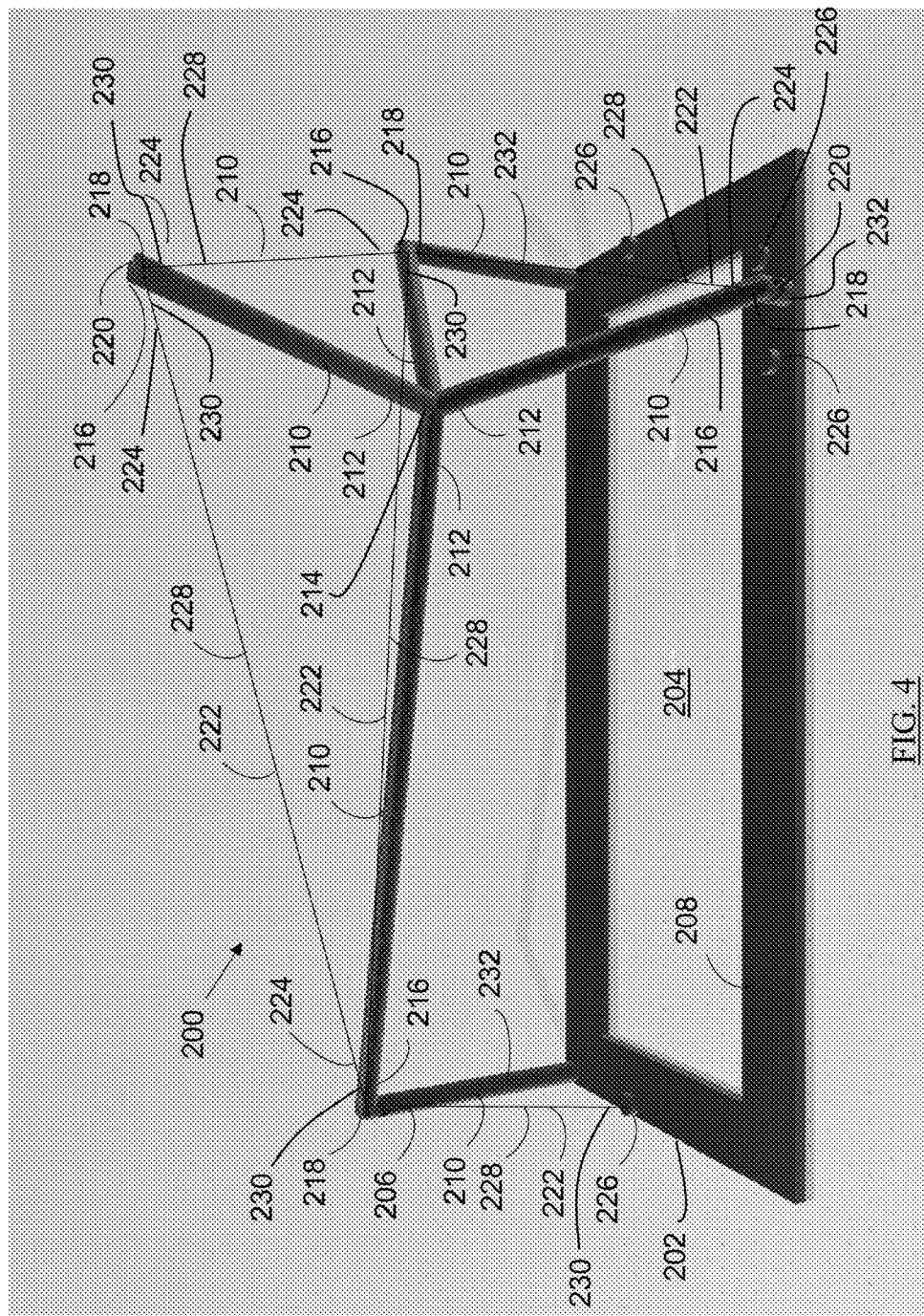
FIG. 4 is a perspective front view of a calibration device in accordance with the present invention.
Figure 5:
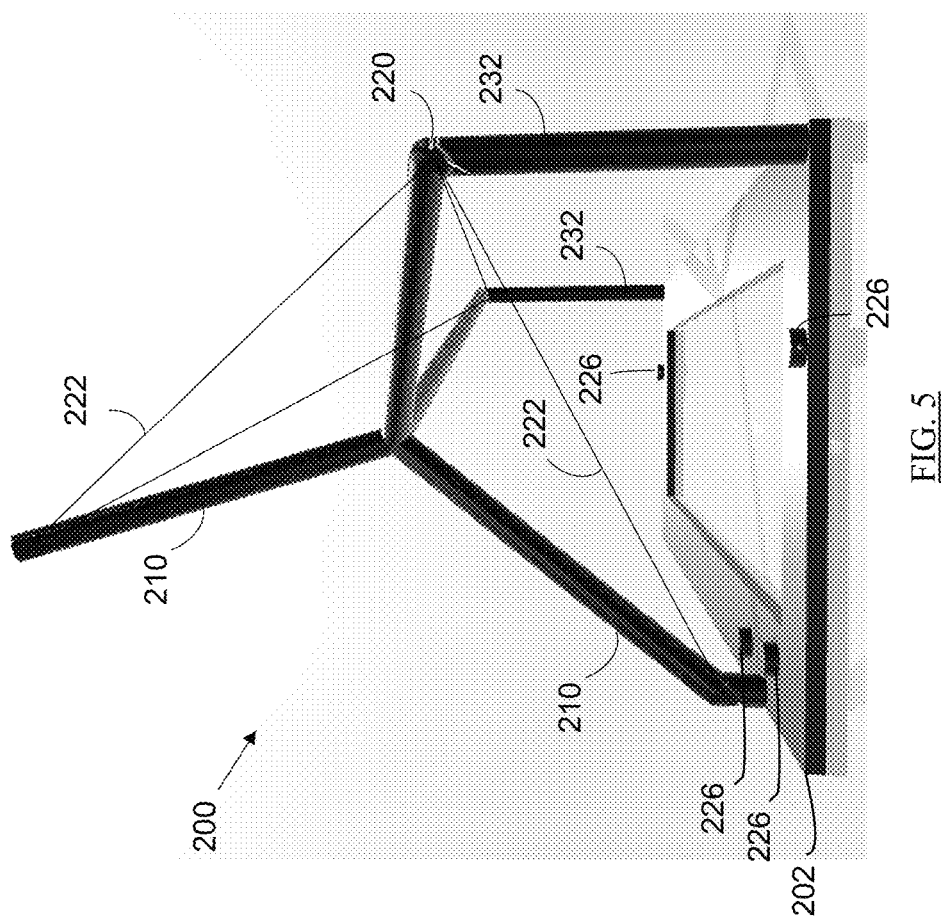
FIG. 5 is a right side view of the calibration device of FIG. 4.
Figure 6:
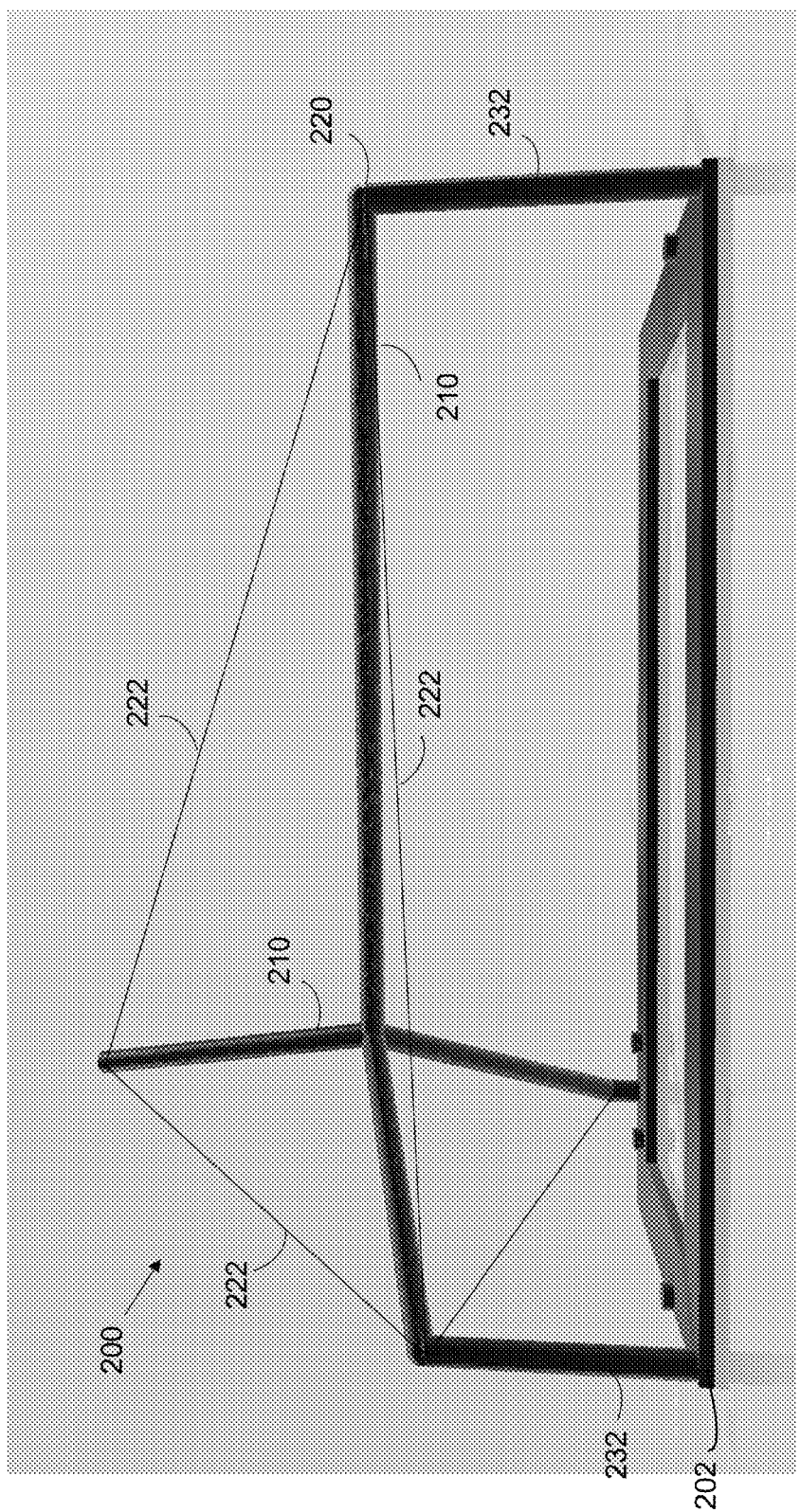
FIG. 6 is a rear view of the calibration device of FIG. 4.
Figure 7:
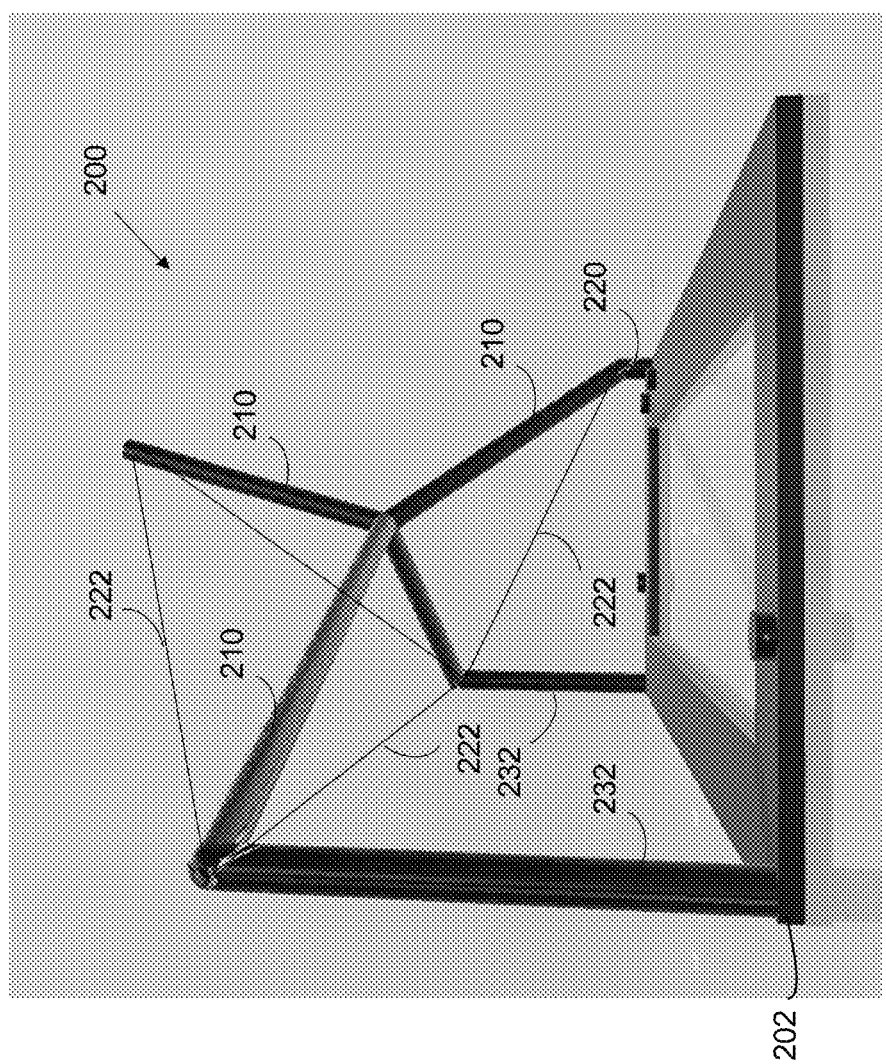
FIG. 7 is a left side view of the calibration device of FIG. 4.
Figure 8:
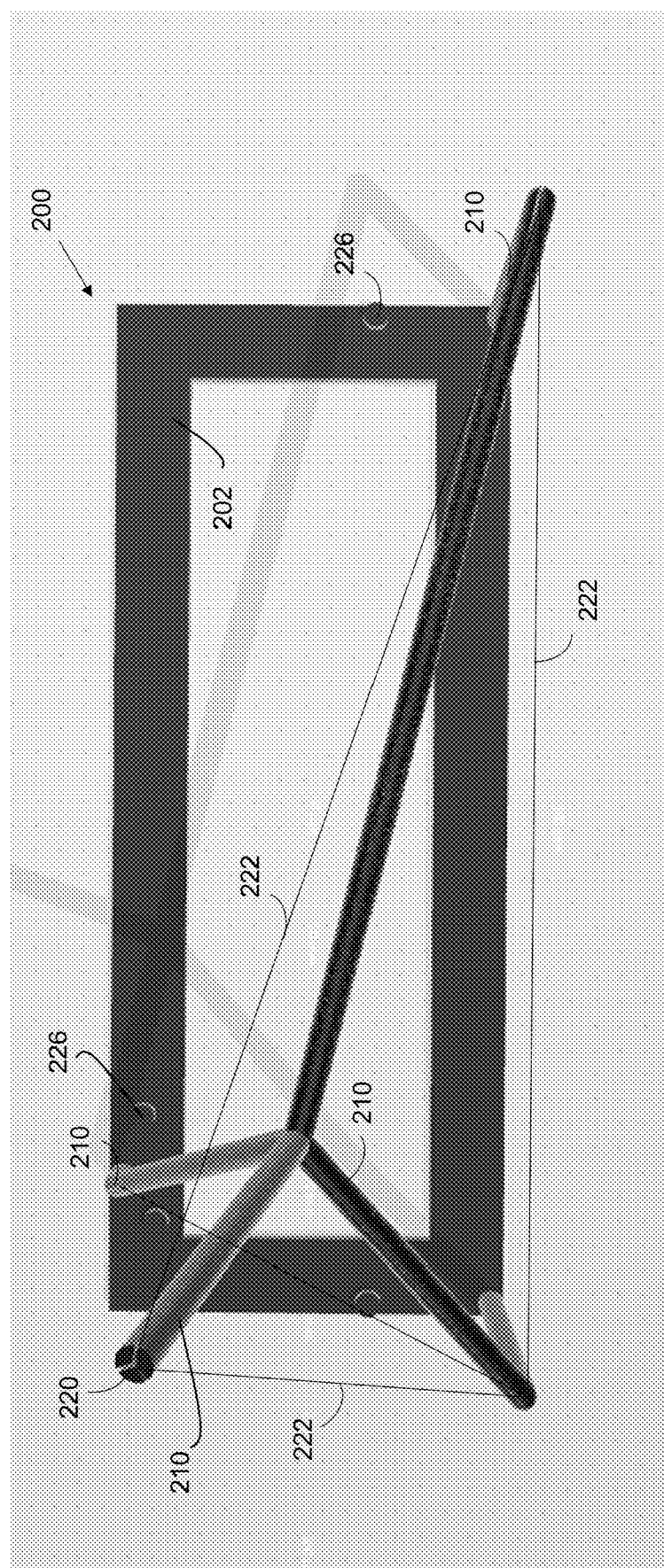
FIG. 8 is a top-down view of the calibration device of FIG. 4.
Figure 9:
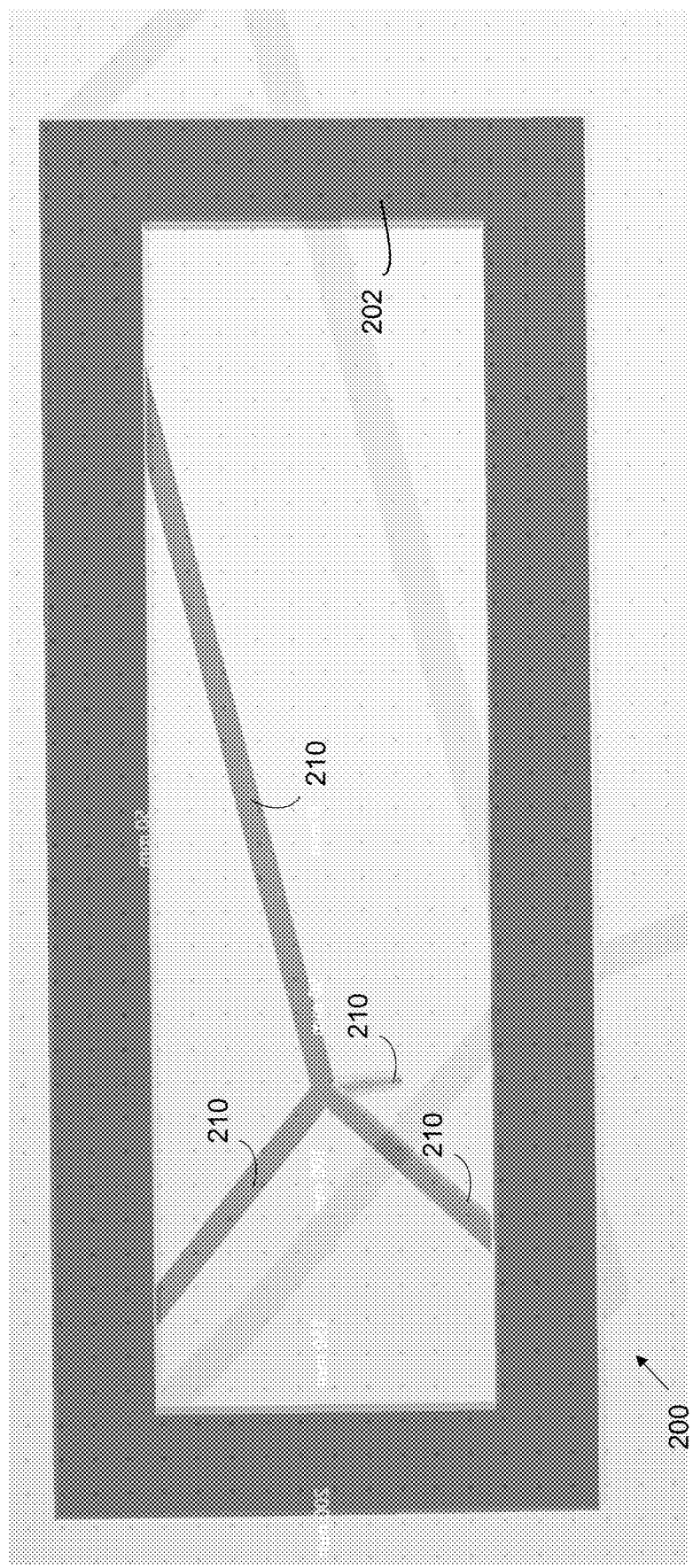
FIG. 9 is a bottom-up view of the calibration device of FIG. 4.

An exemplary calibration device or tool 200 is shown in FIG. 4. Preferably, the calibration device 200 includes a base portion 202 which is preferably rectangular and having an aperture or window 204, preferably also rectangular in shape, passing therethrough. The window 204 permits uninterrupted passage of x-rays from beneath the calibration device 200 and thereby permits an unobstructed view of at least some of the other components of the calibration device 200 further described herein. The calibration device 200 also has a frame portion 206 coupled with an upper surface portion 208 of the base portion 202. The calibration device 200 is preferably composed of a plastic and may be manufactured by any suitable means, such as additive manufacturing.

The frame portion 206 includes a plurality of frame members 210. In an exemplary aspect the frame members 210 are coupled together at a first end portion 212 thereof to form a central portion 214. In said exemplary aspect each of the frame members 210 extend outwardly from the central portion 214 and away from one another to a second end portion 216 thereof. Each of the second end portions 216 preferably includes an attachment portion 218. However, it should be understood that the attachment portions 218 may be found at other locations along the frame member 210. The attachment portions 218 may include a slot 220. The frame portion 206 is adapted as further described herein to support a system of wires 222, each having wire end portions 224. Preferably, the wires 222 are metallic.

In an exemplary aspect, the metallic wires 222 are attached to the base portion 202 of the calibration device at attachment portions or anchor points 226 and extend in between the anchor points 226 through the slots 220 to form the system of wires 222 supported in tension by the frame portion 210. The base portion 202 may include any suitable number of anchor points 226. In an exemplary aspect, the anchor point 226 is a cylinder attached to the base portion 202 and is protruding therefrom.

It should further be understood that although the wires 222 extend through slots 220 of attachment portions 218 and anchor points 226, the wires 222 may be otherwise secured to attachment portions 218 and anchor points 226, such as being inset on the attachment portions 218 or anchor points 226 or wound about the attachment portions 218 and anchor points 226, for example.

The system of wires 222 provides straight edges 228 defined by the wires extending between wire end portions or vertices 230. It is preferable to use metallic wires 222 for the purpose of providing the straight edges 228 because they produce a high-contrast image but which is only a few pixels in width.

The system of wires 222 may be configured to form any structure. It is preferable that the system of wires 222 form a structure in which at least two edges 228 are not parallel to each other. For example, diagonal edges allow good contrast on the dual energy images, which provides better identification of the edges while analyzing the data received by the scans performed on the calibration tool 200. In an exemplary aspect, the system of wires 222 forms a tetrahedral structure in which the four edges 228 are not parallel to each other. However, any other suitable shape formed by the wires 222 may be used.

The frame portion 210 may further include vertical frame members 232 extending vertically from the base portion 202 to couple with the frame members 210. As shown in FIG. 4, for example, three vertical frame members 232 extend vertically from the base portion 202 to couple with three of the frame members 210. Preferably, the vertical frame members 232 are of different lengths. This allows the tetrahedral structure formed by the system of wires 222, or more specifically the "base" of the tetrahedral structure, to be skewed or tilted to an orientation which is not perfectly horizontal. Skewing the tetrahedron positions the wires 222 at different relative positions to the detectors 120 of the detector array 116, 118 thereby providing for different dual-energy output data from wire to wire during a scanning operation and a greater variety of dual-energy data which may be used to obtain calibration information.

The calibration tool 200 as described in accordance with the above preferred aspect includes a rectangular base portion 202 and frame members 210 and a system of wires 222 which form a tetrahedron or tetrahedral shape to provide the geometric features used for calibration. It should be understood that the base portion 202, the frame members 210 and the system of wires 222 may be configured to be of any shape or configuration that would provide geometric features for which appropriate measurements can be taken and which are identifiable in dual-energy data images produced during a scanning operation for the purposes of calibration. Accordingly, the base portion 202 is not limited only to a rectangular configuration nor are the frame members 210 and system of wires 222 limited only to providing a tetrahedral configuration for the system of wires 222.

Figure 10:
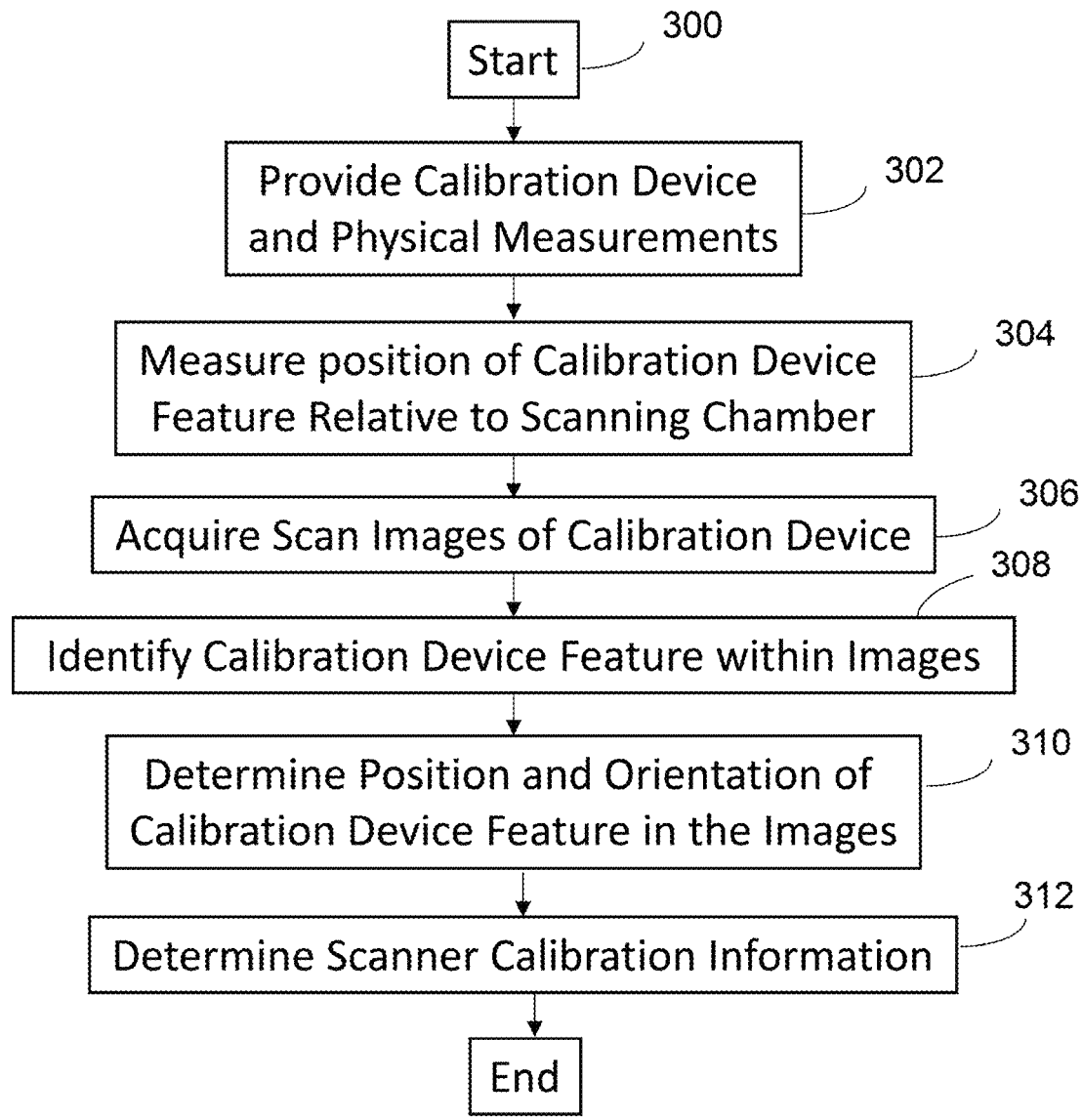
FIG. 10 is a flowchart illustrating the method of one aspect of the present invention; and, FIG. 11 is a flowchart illustrating the method of a second aspect of the present invention.

A first aspect of the method 300 for acquiring at least one x-ray scanning system geometric property in accordance with the present invention is described herein with respect to FIG. 10.

At step 302, the calibration device 200 having at least one geometric feature thereon is provided as are the physical measurements therefor. At step 304, the position of at least one geometric feature of the calibration device 200 relative to the scanning chamber 106 is measured. At step 306, scanned images of calibration device 200 are acquired. At step 308, the representation of the geometric features of the calibration device 200 are identified in the scanned images. At step 310, the position and orientation of the calibration device feature in the image is determined. At step 312, at least one x-ray scanning system property is determined.

Figure 11:
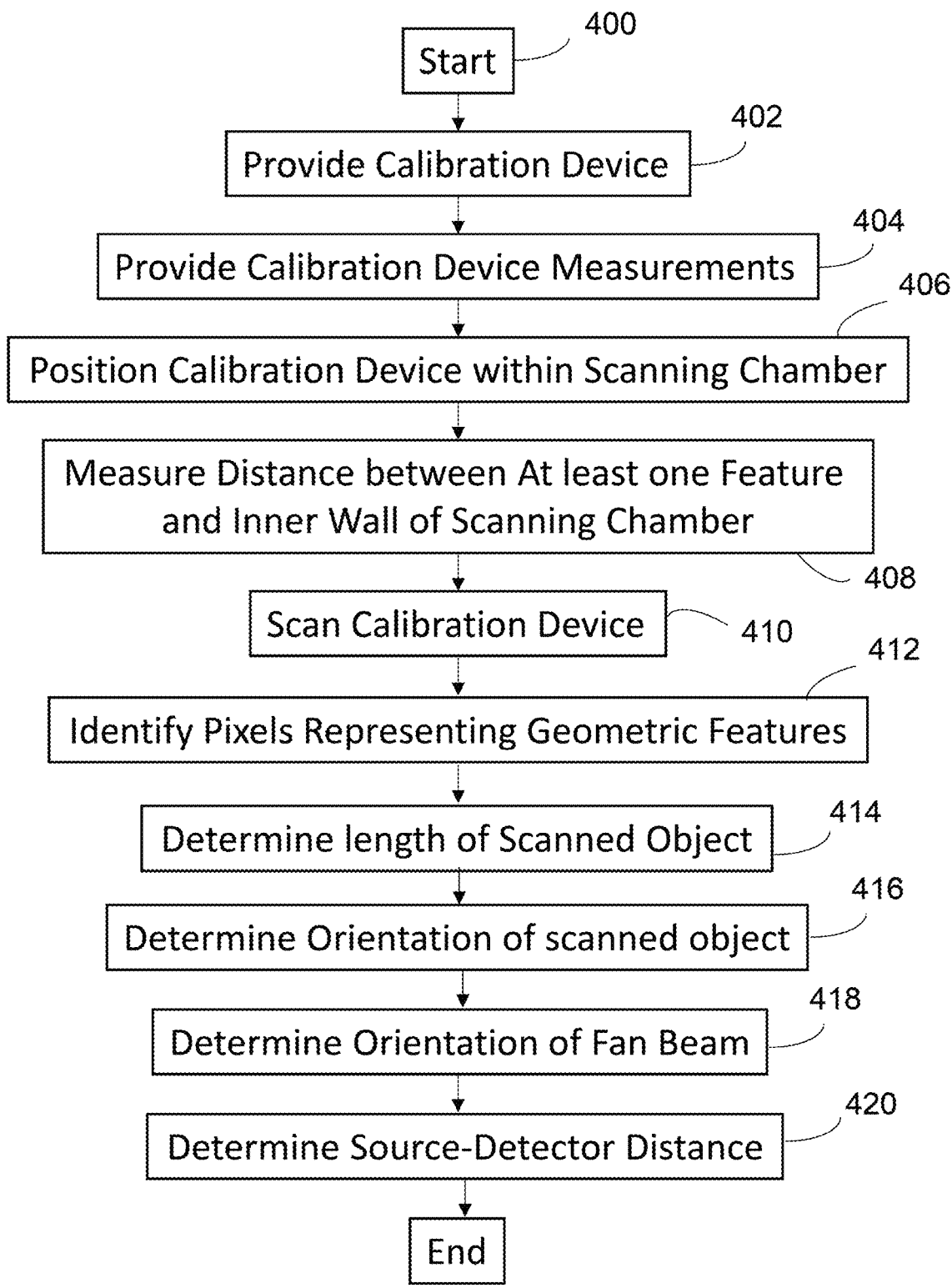

A second aspect of the method 400 for acquiring at least one x-ray scanning system geometric property in accordance with the present invention is described herein with reference to FIG. 11.

At step 402, the calibration device 200 having at least one geometric feature thereon is provided. The properties of the calibration device 200 and the geometric features thereof are known, for example, from measurement of any dimensions of the geometric features, measurements related to the position of the geometric feature relative to other geometric features or with the base of the calibration device, the length and angles of wires, or the positions and angles of wire end portions. The dimensions of the calibration device and its shape with respect to the geometric features may also be measured. These measurements may be taken prior to initiation of the method 400 or subsequent to providing step 402 as shown, for example, in FIG. 11 at step 404.

At step 406, the calibration device 200 is positioned within the scanning chamber 106 of the x-ray scanning device 100. At step 408, a distance between the calibration device 200, and an inner wall of the scanning chamber 106 is determined. Preferably, the determined distance is between at least one feature of the calibration device 200 and an inner wall of the scanning chamber 106. Preferably, the feature from which the distance is measured is a point along one of the wires 222 or at least one of the wire end portions 230. In one aspect, in which the calibration device 200 forms a tetrahedral shape, a horizontal distance between an apex of the tetrahedral shape and the upper inner wall 114 of the scanning chamber 106 of the x-ray scanning device 100 may be measured. Preferably, distances between all features and the inner wall of the scanning chamber 106 are measured.

At step 410, a scanning operation is performed on the calibration device 200. The scanning operation outputs at least one image having pixels representing the geometric features of the calibration device 200. The at least one image, may include a raw data dual-energy image and preferably a plurality of raw data dual-energy images.

At step 412, pixels of the at least one image representing the geometric features of the calibration device 200 are identified. Preferably, the features identified in the at least one image include vertices and edges. The vertices are pixels representing the wire end portions 230 in the image and the edges are pixels extending between the vertices, which are the pixels representing the length of wire 222 extending between the wire ends 230. To locate the vertices and edges, the image archive is searched for pixels which represent metal wire. Step 416 can be performed manually by a user or automatically, using any suitable algorithm.

Where the at least one image includes a dual-energy image, the identification of the features can be based on the analysis of the data of a low energy image, a high energy image or a combination of both. Preferably, the identification of the pixels is performed automatically and in real-time or near real-time.

Although the calibration device 200 is preferably constructed with wires 222 being taut and straight between attachment points, the pixels representing wires 222 may not necessarily be in a straight line in the at least one image due to the geometry of the x-ray scanning device 100. In the vertical dimension of the image, lines may be skewed because of the fan beam. Since the fan beam is fan-shaped, some lines which should be straight may appear in the image as curved lines. Moreover, the fan beam depends on the geometry of the x-ray scanning device, including the position of the detector cards and the position of the source producing the fan beam.

The horizontal dimension of the image is controlled by the displacement assembly which displaces the calibration device 200 through the scanning chamber and across the fan beam. The displacement speed is known and is preferably constant. The pixels collect data for a known period and so it is known what the width of one pixel of the image represents in actual 3D space.

The projection of a scanned object which is "x" pixels wide onto an axis that is parallel with the axis of displacement through the scanning chamber may be used to determine the length of the representation of the scanned object in the image, as at step 414. Such a determination may be made using any suitable algorithm, such as for example, trigonometric calculation using the width of the projection and the angle of the scanned object known from the dimensions of the calibration tool 200.

Preferably, the identified feature represents the edge and vertices formed by one wire 222 of the system of wires 222 of the calibration device 200. Once the pixels representing the wire end portions 230 (i.e., the vertices) are identified, the projections onto the aforementioned axis of displacement may be used to determine the orientation of the wire 222 in the at least one image, as at step 416. This may be repeated for all wires 222 in the system of wires 222, if desired.

The orientation of each fan beam of the x-ray scanning device 100 is determined at step 418. In a preferred aspect, the orientation of each of the fan beam planes is determined simultaneously with the determination of the orientation of the identified feature of the calibration tool 200. This may be done using any suitable algorithm or system of algorithms. Preferably, the algorithm uses a least squares analysis to solve for fan beam angles and angles of the identified feature which minimize a difference between the geometric features of the calibration device 200 as represented by pixels in the at least one image of the calibration tool 200 and the geometric features of the calibration device 200 as represented in the actual calibration tool 200. The difference to be minimized may be a difference in at least one of distance, position and orientation, for example.

Once the orientation of the fan beam is determined, the distance between each source and detector array may be determined, as shown at step 420, using any suitable algorithm.

The methods of the present invention permit for determination of the orientation of the geometric features of the scanned object represented in the images as well as the orientation of the fan beams and the distance between the sources and detector arrays. Accordingly, one or more geometric properties of the scanning system may be determined using the methods described herein.

The calibration device can be taken out of the calibration chamber and the process of steps 402 to 422 may be repeated multiple times to obtain data for different positions and orientation of the calibration device.

While the invention has been described in terms of specific aspects, it is apparent that other forms could be adopted by one skilled in the art. For example, the methods described herein could be performed in a manner which differs from the aspects described herein. The steps of each method could be performed using similar steps or steps producing the same result, but which are not necessarily equivalent to the steps described herein. Some steps may also be performed in different order to obtain the same result. Similarly, the apparatuses and systems described herein could differ in appearance and construction from the aspects described herein, the functions of each component of the apparatus could be performed by components of different construction but capable of a similar though not necessarily equivalent function, and appropriate materials could be substituted for those noted. Accordingly, it should be understood that the invention is not limited to the specific aspects described herein. It should also be understood that the phraseology and terminology employed above are for the purpose of disclosing the illustrated aspects, and do not necessarily serve as limitations to the scope of the invention.

The invention claimed is:

1. A calibration device for use with an x-ray scanning device comprising:
   a base, having an aperture therethrough;
   a frame extending upwardly relative to the base, wherein the base and the frame are integral with each other;
   at least one first attachment portion coupled with at least one of the base or the frame at a first location;
   at least one second attachment portion coupled with at least one of the base or the frame at a second location, wherein the second location is different than the first location; and
   at least one wire extending between the at least one first attachment portion and the at least one second attachment portion.

2. The calibration device of claim 1, further comprising:
   a plurality of first attachment portions, in addition to the at least one first attachment portion, coupled to at least one of the base or the frame at a plurality of third locations;
   a plurality of second attachment portions, in addition to the at least one second attachment portion, coupled to at least one of the base or the frame at a plurality of fourth locations, wherein the plurality of third locations is different than the plurality of fourth locations; and,
   a plurality of wires, in addition to the at least one wire, wherein each of the plurality of wires extends between a corresponding one of the plurality of first attachment portions and a corresponding one of the plurality of second attachment portions.

3. The calibration device of claim 2, wherein:
   the frame comprises a plurality of projections each having coupled therewith at least one of the plurality of first attachment portions and at least one of the plurality of second attachment portions.

4. The calibration device of claim 3, wherein:
   at least two projections of the plurality of projections are joined at end portions of the at least two projections of the plurality of projections.

5. The calibration device of claim 1, wherein the base and the frame are formed by additive manufacturing.

6. The calibration device of claim 1, wherein the base is configured to be supported on a displacement assembly positioned in a scanning chamber of an x-ray scanning device.

7. A calibration device for use with an x-ray scanning device comprising:
   a base, wherein the base comprises an aperture therethrough configured to reduce an obstruction of X-rays passing through the calibration device during scanning;
   a frame extending upwardly relative to the base;

at least one first attachment portion coupled with at least one of the base or the frame at a first location;

at least one second attachment portion coupled with at least one of the base or the frame at a second location, wherein the second location is different than the first location; and at least one wire extending between the at least one first attachment portion and the at least one second attachment portion.

8. The calibration device of claim 7, further comprising:

a plurality of first attachment portions, in addition to the at least one first attachment portion, coupled to at least one of the base or the frame at a plurality of third locations;

a plurality of second attachment portions, in addition to the at least one second attachment portion, coupled to at least one of the base or the frame at a plurality of fourth locations, wherein the plurality of third locations is different than the plurality of fourth locations; and, a plurality of wires, in addition to the at least one wire, wherein each of the plurality of wires extends between a corresponding one of the plurality of first attachment portions and a corresponding one of the plurality of second attachment portions.

9. The calibration device of claim 8, wherein:

the frame comprises a plurality of projections each having coupled therewith at least one of the plurality of first attachment portions and at least one of the plurality of second attachment portions.

10. The calibration device of claim 9, wherein at least two projections of the plurality of projections are joined at end portions of the at least two projections of the plurality of projections.

11. The calibration device of claim 7, wherein the base is configured to be supported on a displacement assembly positioned in a scanning chamber of an x-ray scanning device.

12. The calibration device of claim 7, wherein the base has a rectangular shape.

13. The calibration device of claim 7, wherein the base and the frame are formed by additive manufacturing.

* * * * *